United States Patent [19]

Becker et al.

[11] 4,046,510
[45] Sept. 6, 1977

[54] METHOD AND AN APPARATUS FOR DETERMINING THE INORGANIC CARBON CONTENT OF A LIQUID

[75] Inventors: Wolf-Jurgen Becker, Leverkusen; Jacques Deprez, Frechen; Horst Lehnert, Leverkusen, all of Germany

[73] Assignee: Bayer Aktiengesellschaft, Leverkusen, Germany

[21] Appl. No.: 708,945

[22] Filed: July 27, 1976

[30] Foreign Application Priority Data

Aug. 2, 1975 Germany .................. 2534620

[51] Int. Cl.² ............... G01N 31/12; G01N 33/18
[52] U.S. Cl. ........................ 23/230 R; 23/230 PC; 23/253 PC
[58] Field of Search ......... 23/230 R, 230 PC, 253 PC

[56] References Cited

U.S. PATENT DOCUMENTS

| 3,346,342 | 10/1967 | Miller | 23/253 PC |
| 3,374,064 | 3/1968 | Kolsto | 23/253 PC |
| 3,459,938 | 8/1969 | Stenger et al. | 23/230 PC |
| 3,726,646 | 4/1973 | Kravetz et al. | 23/253 PC |

*Primary Examiner*—Robert M. Reese
*Attorney, Agent, or Firm*—Connolly and Hutz

[57] ABSTRACT

In a process for the determination of the inorganic carbon content of aqueous liquids, the sample to be examined, together with a carbon dioxide-free carrier gas, is introduced into a heated reaction chamber, where it is reacted with crystalline potassium bisulphate and/or a mixture of equal parts of potassium bisulphate and potassium sulphate to form carbon dioxide and water. The $CO_2$ generated is analyzed quantitatively in a $CO_2$ analyzer.

8 Claims, 2 Drawing Figures

METHOD AND AN APPARATUS FOR DETERMINING THE INORGANIC CARBON CONTENT OF A LIQUID

The invention relates to a method for determining the inorganic carbon content of aqueous liquids, in which a sample of the liquid to be analysed is put in a heated reaction chamber together with a carbon dioxide-free carrier gas, the inorganic carbon containing compounds are decomposed with a reagent to form carbon dioxide and the carbon dioxide generated is fed to a $CO_2$ analyser. In addition the invention relates to an apparatus for carrying out the method.

In German Offenlegungsschrift Nos. 2,261,456 and 2,261,449 methods and apparatuses are described for the pyrolytic determination of the total carbon content (TC = total carbon) of aqueous solutions, in particular waste waters. The total carbon content is composed of the organic (TOC = total organic carbon) and the inorganic (TIC = total inorganic carbon) carbon content. In many surface waters, communal waste waters etc, the inorganic carbon content (carbonate hardness) is often in the same order of magnitude as the organic carbon content. For this reason it is necessary to determine both values in the analysis.

German Auslegeschrift No. 1,598,361 describes a method for determining the inorganic carbon content of an aqueous dispersion. In this process a specific quantity of the liquid to be analysed is injected into a heated zone containing a body having an acidic surface which is reactive towards carbonate. A carbon dioxide-free carrier gas flow then transports the gas mixture formed to a carbon dioxide analyser connected downstream. The heated zone is at a temperature above 100° C. However the temperature should not be so high that the organic components contained in the liquid decompose. The reactive body with the acidic surface comprises quartz chips coated with phosphoric acid. A manual analysis unit working by this method is commercially available. However, this device displays relatively large spreads of the measurement values for the injection of a liquid of constant carbonate hardness. The reproducibility of the measurement values thus leaves much to be desired. The relatively poor reproducibility is caused by the liquid sample always being sprayed in the reaction chamber onto the same point on the reactive body. In this way this point becomes depleted of reactive substance. Re-supply, e.g. from other points of the reactive body, is not possible. The reagent (phosphoric acid) is therefore so heavily diluted at the injection point after a long period of use that the reaction can no longer take place completely. A further disadvantage of this device is that a part of the liquid reaches the walls of the reaction chamber. As a result of the higher temperature of the reaction chamber it evaporates there immediately and the carbonates are precipitated in solid form and are thus lost to the analysis.

The object of the invention is to improve the method described above in respect of measurement accuracy and reproducibility. A measurement accuracy of 2% (relative to the measurement value) is desired. An important step in this direction was the recognition that the reagent should be supplied in excess and that the quantity of liquid to be analysed should reach the reagent in as short a time as possible. According to the invention, there is provided a method for determining the inorganic carbon content of aqueous liquids, wherein a sample of the liquid to be analysed, together with a carbon dioxidefree carrier gas, is introduced into a heated reaction chamber containing as a reagent crystalline potassium bisulphate and/or a mixture of equal parts of potassium bisulphate and potassium sulphate, with which the sample is reacted to form carbon dioxide and water and the carbon dioxide is fed to a carbon dioxide analyser. The potassium bisulphate which reacts as an acid drives out the inorganically bonded carbon (carbon hardness) of a liquid as carbon dioxide.

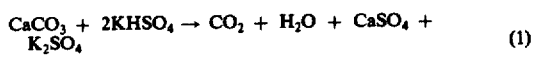

(1)

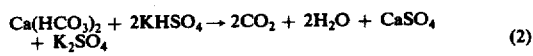

(2)

The traces of free sulphuric acid, $H_2SO_4$, contained in the potassium bisulphate, $KHSO_4$, can be bonded by potassium sulphate $K_2SO_4$, which is either added to the potassium bisulphate or which is present in a subsequent reaction stage.

(3)

Above 100° C, the reactions according to equations (1) and (2) take place quickly and almost quantitatively. A reaction temperature of 140° C has proved to be the optimum.

In order to prevent the reaction zone being cooled by the carrier gas, the carrier gas may be heated before entering the reaction chamber to the temperature prevailing in the chamber.

According to the invention, there is also provided an apparatus for determining the inorganic carbon content of aqueous liquids, comprising a reaction chamber, means for heating the reaction chamber and means for producing a carbon dioxide-free carrier gas and a carbon dioxide analyser connected to the reaction chamber, wherein the reaction chamber contains a plurality of layers of reagent of differing composition, which layers fill the reaction chamber to the level of a perforated screen.

Advantageously, as seen in the direction of flow, the first layer comprises potassium bisulphate and the second layer comprises a mixture of equal parts of potassium bisulphate and potassium sulphate. A further improvement is achieved by a third layer of potassium sulphate. In this way sulphur trioxide, $SO_3$, and hydrochloric acid, HCl, which may be produced in the thermal decomposition of accompanying substances in the sample liquid, are absorbed, whereby the subsequent analysis device is protected.

According to a preferred embodiment of the invention, the crystalline potassium bisulphate or potassium sulphate is applied onto an inert and porous granulate. Advantageously the porous granulate coated with potassium bisulphate is mixed with crystalline potassium bisulphate. The special design of the reaction chamber according to the invention permits fitting in the analysis device both in the horizontal and in the vertical position.

The advantages obtained with the invention are in particular that the point of the reactive substance which comes into contact with the liquid sample to be analysed can no longer be depleted. This results in a substantial improvement or reproducibility. In addition the service life and long term stability are substantially improved. An important advantage is also that the reaction chamber contains no liquid phase, so that losses of acid by evaporation can no longer occur. In addition, it has been shown that the walls of the reaction chamber are practically no longer attacked. Finally, the reaction capacity of the $KHSO_4$ for the same mass relative to comparable reaction chambers is greater.

Two embodiments of the invention are illustrated in the drawing and described in more detail in the following.

Figure 1:
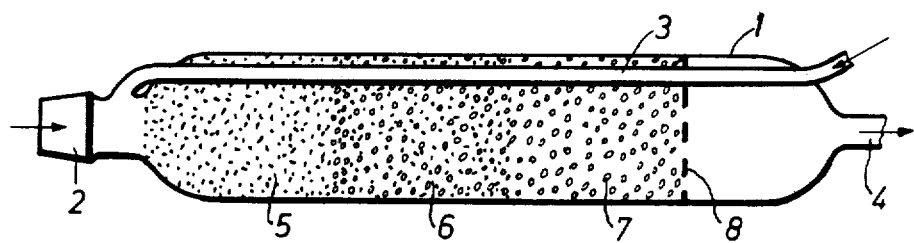
FIG. 1 shows a horizontal reaction chamber.

According to FIG. 1 the dosing of the liquid sample to be analysed into the horizontally lying reaction chamber 1 takes place via the feed pipe 2. For manual dosing, the feed pipe 2 is sealed by a rubber penetrating cap. For automatic dosing the feed pipe 2 opens into a smooth section on which a dosing valve is located. A suitable dosing valve is described for example in German Offenlegungsschrift No. 2,261,449.

The reaction chamber 1 is located in tubular electric furnace, which maintains the reaction chamber at a temperature of 140° C. A metal tube between the heating furnace inner wall and the reaction chamber 1 ensures that the whole reaction chamber is at the same temperature. The temperature profile of a commercially available tubular furnace displays a higher temperature in the centre of the furnace than at the openings. The metal tube (copper) provides that the heat is conducted to the chamber openings. The reagent in the reaction chamber should as far as possible have the same temperature at all points. In the event of local temperature fluctuations, the reaction takes a different course at different locations. As a result a spread of the measurement values may arise.

In order to prevent the reaction zone at the feed pipe 2 being cooled by the normally cooler carrier gas, the carrier gas is passed in a separated pipe 3 through the reaction chamber, heated up and fed at the feed pipe 2 into the interior of the reaction chamber 1. Atmospheric air is generally used as the carrier gas. The carbon dioxide contained therein in gas form and any hydrocarbon compounds present are removed in a separate air preparation section until only a small constant residue remains. The air preparation section comprises for example Zeolith adsorbers and a pre-combustion chamber arranged between them. After them there is located a pressure regulator with regulator valve to provide a constant carrier gas pressure.

The carbon dioxide-free and preheated carrier gas, together with the liquid sample to be analysed, passes through the feed pipe 2 into the interior of the reaction chamber 1. Here the reaction to form carbon dioxide and water takes place. The temperature of the reaction chamber at 140° C is sufficiently low that the organic carbon compounds do not decompose. The carbon dioxide generated in the reaction chamber 1 thus comes exclusively from the inorganic carbon compounds (carbonates) of the sample. This carbon dioxide together with the carrier gas is forced through the reaction chamber 1 by the prevailing over-pressure and fed via the outlet pipe 4 to a carbon dioxide analyser. A suitable carbon dioxide analyser is for example a commercially available non-dispersive IR-analyser. The $CO_2$ concentration measured here is a measurement for the carbonate hardness of the sample under investigation.

Potassium bisulphate is used as the reagent. In order to prevent sulphuric acid leaving the reaction chamber, the reagent comprises a plurality of layers. According to FIG. 1 the active first layer 5 consists of potassium bisulphate $KHSO_4$, the second layer 6 of a mixture of equal parts of potassium bisulphate $KHSO_4$ and potassium sulphate $K_2SO_4$ and the third layer 7 of potassium sulphate $K_2SO_4$. The third layer ends in the region of the outlet zone and is limited by a perforated screen 8 or coarse-mesh frit located in the reaction chamber.

According to a preferred embodiment, the reagent comprises potassium bisulphate ($KHSO_4$), applied to an inert and porous pumice granulate. For this purpose, 1 part potassium bisulphate $KHSO_4$ is dissolved in 2 parts distilled water and 1 part pumice granulate is boiled in the solution for 3 to 4 hours in a reflux distilling apparatus. The granulate when cooled is dried in a rotary evaporator at approximately 100° C. After this preparation the potassium bisulphate $KHSO_4$ is present on the pumice granulate in the finest distribution. Pumice granulate can be coated with potassium sulphate $K_2SO_4$ by a similar process. The pumice granulate coated with $KHSO_4$ forms the first active layer 5 in the reaction chamber. The second layer 6 in this case consists of a mixture of equal parts of potassium bisulphate $KHSO_4$ and potassium sulphate $K_2SO_4$ applied to pumice granulate. The third layer 7 consists of pumice granulate coated with potassium sulphate $K_2SO_4$. To raise the potassium bisulphate content in the first active layer 5, crystalline potassium bisulphate $KHSO_4$ can be added to the pumice coated with potassium bisulphate $KHSO_4$.

Figure 2:
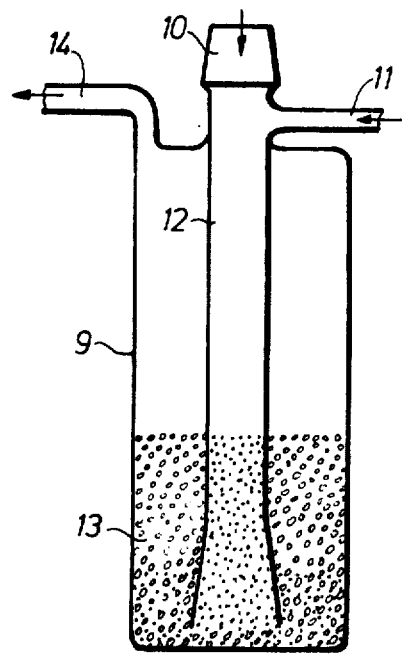
FIG. 2 shows a vertical reaction chamber.

According to FIG. 2 the liquid sample to be analysed is dosed into a vertical reaction chamber 9 via a feed pipe 10. Similarly to the first embodiment, manual or automatic dosing is possible using an injection valve. The reaction chamber 9 is heated in the same manner as in the first embodiment according to FIG. 1 with a tubular furnace. In contrast to the first embodiment, the carrier gas is preheated in a separate furnace. The inlet 11 for the carrier gas is located on the feed pipe 10 outside the reaction chamber 9.

The carrier gas charged with the sample to be analysed is passed through the reagent 13 by means of the guide pipe 12. The guide pipe 12 ends in the region of the floor of the reaction chamber 9. This ensures that the liquid sample to be analysed takes the longest possible path through the reagent 13, without thereby creating dead volumes. The carrier gas and the carbon dioxide generated from the inorganic carbon compounds (carbonates) are compressed through the chamber by the prevailing overpressure and fed through the outlet pipe 14 to the carbon dioxide analyser.

Similarly to the first embodiment, the reagent 13 consists of $KHSO_4$ or pumice granulate coated with $KHSO_4$. As in the first embodiment the layering of the reagent has also proved valuable with the vertically standing reaction chamber. The guide pipe 12 is filled with pure potassium bisulphate $KHSO_4$ or pumice granulate coated with potassium bisulphate $KHSO_4$, while the outer space between the guide pipe 12 and the chamber wall 9 is filled with pure potassium sulphate $K_2SO_4$ or pumice granulate coated with potassium sulphate. The transitional zone at the bottom of the chamber can again also consist of a mixture of equal parts potassium bisulphate $KHSO_4$ and potassium sulphate $K_2SO_4$ or potassium bisulphate $KHSO_4$ and pumice coated with potassium sulphate $K_2SO_4$.

A common feature of both embodiments is the recognition that the reagents should always be available in high concentration in the reaction with the sample to be analysed and that the sample, once dosed, should immediately come into contact with the reagent. Only under these conditions can the required accuracy of analysis and reproducibility be achieved.

What we claim is:

1. A method for determining the inorganic carbon content of aqueous liquids, wherein a sample of the liquid to be analysed, together with a carbon dioxide-free carrier gas, is introduced into a heated reaction chamber containing as a reagent crystalline potassium bisulphate and/or a mixture of equal parts of potassium bisulphate and potassium sulphate, with which the sample is reacted to form carbon dioxide and water and the carbon dioxide is fed to a carbon dioxide analyser.

2. A method as claimed in claim 1, wherein the potassium bisulphate, and the potassium sulphate, if present, is applied to an inert and porous granulate.

3. A method as claimed in claim 1, wherein the potassium bisulphate is present as a mixture of a porous granulate coated with potassium bisulphate and crystalline potassium bisulphate.

4. A method as claimed in claim 1, wherein the carrier gas is heated to the temperature prevailing in the reaction chamber before entering the reaction chamber.

5. A method as claimed in claim 1, wherein the carrier gas, together with the sample and/or the reaction products of the reaction between the sample and the reagent, is passed successively through a first layer comprising potassium bisulphate and a second layer consisting of a mixture of equal parts of potassium bisulphate and potassium sulphate.

6. A method as claimed in claim 5, wherein the carrier gas, together with the reaction products of the reaction between the sample and the reagent is passed through a third layer comprising potassium sulphate.

7. A method as claimed in claim 1, wherein the temperature in the reaction chamber is above 100° C.

8. A method as claimed in claim 6, wherein the temperature in the reaction chamber is approximately 140° C.

* * * * *